(12) United States Patent
Oben

(10) Patent No.: US 7,537,790 B2
(45) Date of Patent: May 26, 2009

(54) METHOD AND COMPOSITION FOR REDUCING BODY WEIGHT AND IMPROVING CONTROL OF BODY LIPIDS

(75) Inventor: Julius Oben, Yaounde (CM)

(73) Assignee: Gateway Health Alliances, Inc., Fairfield, CA (US)

( * ) Notice: Subject to any disclaimer, the term of this patent is extended or adjusted under 35 U.S.C. 154(b) by 0 days.

(21) Appl. No.: 11/557,916

(22) Filed: Nov. 8, 2006

(65) Prior Publication Data

US 2007/0065523 A1 Mar. 22, 2007

Related U.S. Application Data

(62) Division of application No. 11/383,947, filed on May 17, 2006, now abandoned.

(60) Provisional application No. 60/682,045, filed on May 17, 2005.

(51) Int. Cl.
*A01K 65/00* (2006.01)
*A61K 36/00* (2006.01)

(52) U.S. Cl. .................. 424/725; 424/776; 514/909

(58) Field of Classification Search .................. None
See application file for complete search history.

(56) References Cited

U.S. PATENT DOCUMENTS 6,216,707 B1 4/2001 Pauly

2004/0162352 A1 * 8/2004 Chen et al. .................. 514/563

OTHER PUBLICATIONS

Adamson, I. et al., A supplement of Dikanut (Irvingia gabonesis) improves treatement of type II diabetics. West Afraican Journal of Medicine, 9 (2): 108-115, 1990.*
Okolo et al., Analgesic effect of Irvingia gabonensis stem bark extract. Journal of Ethnopharmacology 45: 125-129, 1995.*
Adamson et al., A supplement of dikanut (Irvingia gabonesis) improves treatement of type II diabetics, West Afraican Journal of Medicine, 9 (2): 108-115, 1990.*
Ejiofor, Developing improved methods of processing and utilization of kernels of Irvingia-gabonensis-var-gabonesis and Irvingia-gabonensis-var-excelsa, International Tree Crops Journal, (1987) vol. 4, No. 4, pp. 283-290.*

* cited by examiner

*Primary Examiner*—Michele Flood
*Assistant Examiner*—Qiuwen Mi
(74) *Attorney, Agent, or Firm*—Steve P. Hassid; Greenberg Traurig, LLP

(57) ABSTRACT

Methods and composition using plants from the Irvingiaceae family to reduce or prevent one or more symptoms of Syndrome X in a mammal and provide numerous other health related benefits. Methods and compositions using the Irvinga gabonensis plant to reduce lipid levels, BMI and body weight, blood pressure, triglyceride levels, total amount of stored in the body, cholesterol levels, salivary and pancreatic alpha-amylase activity and pancreatic lipase activity, LDL cholesterol, to increase HDL cholesterol, to control blood glucose and to prevent or reduce the effects of insulin resistance, diabetes, and heart disease.

16 Claims, 1 Drawing Sheet

Effect Of *Ig* On Blood Lipids And Liver Cholesterol $p<0.05$; $**p<0.01$ compared to positive control

METHOD AND COMPOSITION FOR REDUCING BODY WEIGHT AND IMPROVING CONTROL OF BODY LIPIDS

RELATED APPLICATIONS

This application is a divisional of U.S. patent application Ser. No. 11/383,947, filed on May 17, 2006, which claims the benefit of and priority to U.S. Provisional Application Ser. No. 60/682,045, filed May 17, 2005, the contents of which are incorporated by reference herein in their entireties.

BACKGROUND

This present disclosure relates generally to method and related composition using plants of the Irvingiaceae family (Ig) to provide numerous health benefits, and more particularly, to the use of Ig and extracts of Ig to control body lipid levels, reduce body weight and prevent or reduce other symptoms associated with Syndrome X, a common metabolic disorder.

Syndrome X is a term that is commonly known in the art that typically refers to a group of health related problems that can include insulin resistance, which is the bodies inability to properly deal with dietary carbohydrates, abnormal blood fats and lipid levels, being overweight, and having high blood pressure.

Insulin resistance is a condition in which the body becomes resistant to its own insulin. The affected individual compensates by releasing more insulin, which can ultimately lead to an increased risk of a variety of symptoms, including, but not limited to obesity, diabetes and heart disease. Accordingly, the development of strategies to prevent or control Syndrome X and to prevent and reduce the symptoms that cause Syndrome X, which include, among other things, insulin resistance, are worthwhile.

Avoiding weight gain from adolescence to middle age is known to reduce cardiovascular morbidity and mortality. Despite much debate in the past regarding the influence of obesity on health and the benefits of maintaining normal weight, it is generally accepted that changes in weight correlate to changes in several atherogenic risk factors.

Even with control of weight, many people can still develop symptoms associated with Syndrome X, all of which are highly undesirable. Therefore, treatments that reduce or prevent the symptoms associated with Syndrome X are needed.

No known method or composition has been entirely effective at reducing weight, improving control of body lipids or preventing symptoms associated with Syndrome X. Therefore, improved methods and compositions that prevent or reduce the symptoms of Syndrome X and provide other health related benefits are needed. The present disclosure fulfils these needs and provides for further advantages.

SUMMARY

The present disclosure resides in the use of plants of the Irvingiaceae (Ig) family and their extracts to provide numerous health benefits, including, but not limited to, providing improved metabolic control of lipids, reducing weight, preventing Syndrome X and reducing and preventing symptoms commonly associated with Syndrome X.

The methods and compositions of the present disclosure provide numerous health related benefits and advantages. Any example of some of the benefits and advantages provided include: 1) preventing Syndrome X 2) reducing or preventing symptoms associated with Syndrome X, 3) controlling blood lipids by reducing the concentration of circulating triglycerides, total cholesterol, and LDL cholesterol, 4) increasing HDL-cholesterols, 5) controlling and improving blood pressure levels by reducing systolic and diastolic blood pressure, 6) reducing body mass index (BMI), 7) reducing the percentage of fat present in body as stored fat, 8) inhibiting the activity of α-amylase in the saliva as well as in the pancreas, 9) inhibiting the activity of pancreatic lipase, and 10) bringing about the fasting and post-prandial control of blood glucose levels.

DETAILED DESCRIPTION OF PREFERRED EMBODIMENTS

Figure 1:
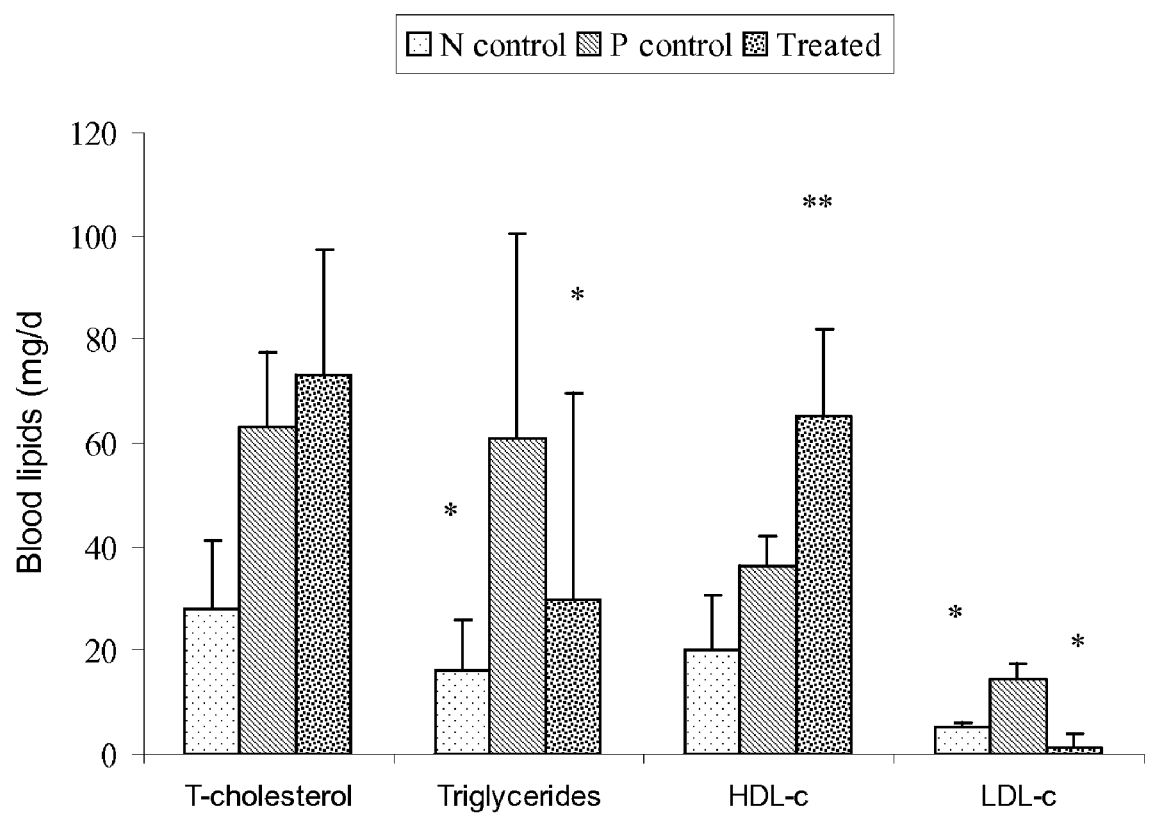
FIG. 1 is a bar graph summarizing the results of our experiments on the effects of Ig supplementation on liver cholesterol, triglyceride, LDL and HDL levels in the Guinea pigs.

Obesity is of major primary care concern and is targeted as an international health objective in Healthy 2000, which seeks to reduce the prevalence of obesity to less than 20%. In the last 10 years, the number of overweight people has increased from 26 to 34%. Conventional dietary and behavioral treatment have failed in long-term management. Traditional dietary strategies used to manage obesity include maintaining a high fiber/low carbohydrate and fat diet. The beneficial effect of dietary fiber in the management of obesity is not well established, since their mechanism of action is not known. The discovery of new medicinal plants has led to the creation of potential drugs that modify feeding behavior and metabolism and may therefore have application in weight management. These plants may also have a positive effect on a variety of other health related factors and the symptoms associated with Syndrome X.

Ig (Aubry-Lecomte ex O'Roke Baill) belongs to Irvingiaceae family. The Irvingia tree is commonly known as bush mango, dikanut or African mango. The flesh of the Ig fruit is consumed, but the most important part of the fruit is the kernel, which is used, in fresh or dried forms in cooking, to add flavoring and consistency to many (typically African) dishes. Ig contains 50% fat, 26.4% total carbohydrate, 2.3% ash, 7.5% crude protein and 14% fiber. In an effort to determine the effect Ig and Ig extracts have on a variety of health related factors and symptoms associated with Syndrome X, various tests investigating its effects on these factors were performed.

Effects of Ig in Humans

It is well known that dietary fibers are frequently used for the treatment of obesity. To determine the effect of Ig on weight, a study was performed to evaluate the efficacy of Ig seeds in the management of weight and obesity. The study was carried out as a double blind randomized study involving 40 male and female obese human subjects having a mean age 42.4 years. Twenty-eight subjects received 1.05 g of Ig three times a day for one month while twelve subjects were given a placebo (P) in following the same schedule. During the one-month study period, all subjects were on a normocaloric diet evaluated every week by a dietetic record book.

More specifically, a total of 40 obese subjects aged between 19 and 55 years were selected for the experiment from a group responding to a radio advertisement. After physical examination and laboratory screening tests, diabetics, pregnant and lactating women were excluded. None of these subjects took any weight reducing medication and none was following any specific diet. The purpose, nature and potential risks of the study were explained to all patients and a written informed consent was obtained before their participation. The local research ethics committee approved the experimental protocol.

The experiment was as a randomized, double blind placebo-controlled crossover design, and consisted of a 4-week treatment period. Subjects were given two different types of capsules containing 350 mg of Ig seed extract (active formulation) or oat bran (placebo). Three capsules were taken three times daily, one-half hour before meals (a total daily amount of 3.15 g of Ig seed extract) with a glass of warm water. Capsules were identical in shape, color and appearance, with neither patients nor researchers knowing what capsule they received. During the experimental period, subjects were examined weekly, with their body weight, body fat, waist and hip circumferences recorded each time. Subjective findings such as increased or decreased appetite, feeling of lightness and gastrointestinal pains were individually noted. Side effects of the active extract, if any were also solicited and noted during each visit. The subjects were also interviewed about their physical activity and food intake during the trial, and were instructed to eat a low fat diet (1800 Kcal) as well as keep a record for seven consecutive days (using household measurements).

To determine the efficacy of the method and composition of the present invention, anthropometric measurements were done at each visit, with body weight and body fat (impedance measurement using a TANITA™ monitor Scale) measurements on fasted (12 hour) subjects wearing light clothing. Waist and hip circumferences were measured by soft non-stretchable plastic tape on the narrowest and the widest parts of the trunk.

To determine the effect of Ig on various body lipids, elevated and abnormal levels of which are symptoms of Syndrome X, blood samples were also collected from the subjects after a twelve hour overnight fast into heparinized tubes at the beginning of the study, after two weeks and at the end of the four weeks of treatment. The concentrations of total cholesterol, triglycerides, HDL-cholesterol, LDL-cholesterol and glucose, in plasma, were measured using a commercial diagnostic kit (Cholesterol infinity, triglycerides Int, EZ HDL™ cholesterol, EZ LDL™ cholesterol, Glucose Trinder, respectively) from SIGMA Diagnostics.

Results of Ig Supplementation in Humans

At the end of the study, the mean body weight of the group of subjects that received Ig (IG group) decreased by an unexpected $5.26\pm2.37\%$ ($p<0.0001$) whereas the mean body weight of the group of subjects that received the placebo decreased by $1.32\pm0.41\%$ ($p<0.02$). The difference observed between the Ig and the placebo groups was significant ($p <0.01$). The results of our experiments demonstrating the effects of Ig supplementation on weight and body fat are summarized in Table 1 below. Ig supplementation also demonstrated significant decreases in systolic and diastolic blood pressure. The results of our experiments demonstrating the effects of Ig supplementation on blood pressure are summarized in Table 2 below. Surprisingly, our experiments also demonstrated that Ig supplementation provides significant decreases in total cholesterol, LDL-cholesterol and triglycerides levels, and a significant increase in HDL-cholesterol levels. As expected, the placebo group did not manifest any significant changes in any of these blood lipid components.

A chart summarizing the results of our experiments on Ig's effects on weight and body fat (expressed as mean±SEM except for anthropometric measurements) is provided in Table 1 below. Paired Student's t-test was carried out on the start and end values of placebo and Ig capsules and also on the differences between the placebo and Ig crude extract.

Effect of Ig Crude Extract on Body Weight Body Fat, and Waist and Hip Circumferences

TABLE 1

| | | Treatment period (weeks) | | |
|---|---|---|---|---|
| | | 0 | 2 | 4 |
| Weight (kg) | Active | 105.10 ± 16.98 | 102.3 ± 17.06 | 101.01 ± 16.63 |
| | placebo | 79.43 ± 9.83 | 79.43 ± 9.83 | 79.33 ± 10.63 |
| Body fat (%) | Active | 46.11 ± 4.4848 | 46.5 ± 3.68 | 45.34 ± 3.52 |
| | placebo | 40.58 ± 3.49 | 40.58 ± 3.9 | 40.3 ± 3.8 |
| Waist (cm) | Active | 112.76 ± 20.5 | 109.7 ± 20.4 | 106.6 ± 20.79 |
| | placebo | 81.1 ± 7.1 | 81.91 ± 7.91 | 81.25 ± 7.52 |
| Hip (cm) | Active | 125.69 ± 11.34 | 122.92 ± 10.67 | 121.15 ± 10.39 |
| | placebo | 122.2 ± 10.7 | 122.2 ± 10.7 | 121.5 ± 10.9 |

Table 1 demonstrates that the indicated dose of Ig induced a decrease in weight of $2.91\pm1.48\%$ ($p<0.0001$) after two weeks and $5.6\pm2.7\%$ ($p<0.0001$) after one month. Although the percentage of body fat was not significantly reduced with both placebo and Ig, the waist circumference ($5.07\pm3.18\%$; $p<0.0001$), and hip circumference ($3.42\pm2.12\%$; $p<0.0001$) were significantly reduced by Ig. A reduction of $1.32\pm0.41\%$ ($p<0.02$) and $2.23\pm1.05\%$ ($p<0.05$) was observed with the placebo after two and four weeks respectively of treatment. Obesity, and more specifically, central obesity, is an accepted symptom of Syndrome X that can be prevented or reduced with Ig supplementation in accordance with th teachings of the present disclosure.

Effect of Ig on Systolic (SBP) and Diastolic (DBP) Blood Pressure

TABLE 2

| | | Treatment period (weeks) | | |
|---|---|---|---|---|
| | | 0 | 2 | 4 |
| SBP (mmHg) | Active | 136.41 ± 19.57 | 132.66 ± 18.48* | 132.83 ± 17.97* |
| | placebo | 134 ± 5.05 | 121.5 ± 5.89 | 123.83 ± 2.92 |
| DBP (mmHg) | Active | 98.5 ± 19.52 | 97.5 ± 22.80 | 94.08 ± 11.07 |
| | placebo | 93.50 ± 10.31 | 93.83 ± 7.41 | 91.5 ± 6.53 |

Values are means ± sem. Significant differences were at *P < 0.001 by comparison to the placebo group As table 2 demonstrates, starting from the second week of supplementation, subjects that received Ig showed significantly reduced systolic blood pressure levels. High blood pressure is an accepted symptom of Syndrome X which can be prevented or reduced by supplementation with Ig in accordance with the teachings of the present disclosure.

Effect of Ig on Blood Total Cholesterol (TC), Triglyceride (TRI), High Density Lipoprotein Cholesterol (HDL-C), Low Density Lipoprotein Cholesterol (LDL-C) and Glucose

TABLE 3

|         |         | T-cholesterol | TRI | HDL-c | LDL-c | LDL/HDL | T-cho/HDL | GLUCOSE |
|---------|---------|---------------|-----|-------|-------|---------|-----------|---------|
| Active  | Initial | 215 ± 55.12   | 162 ± 33.15 | 61.23 ± 20.36 | 121.37 ± 36.3 | 1.98 ± 1.78 | 3.51 ± 2.70 | 3.8 ± 1.92 |
|         | Final   | 130.68 ± 39.5 | 89.22 ± 55.63 | 89.9 ± 28.44 | 66.08 ± 34.27 | 0.735 ± 1.20 | 1.45 ± 1.38 | 2.57 ± 1.03 |
| placebo | Initial | 163.70 ± 25.32 | 130.65 ± 37.82 | 31.38 ± 25.21 | 105.06 ± 11.86 | 5.05 ± 3.94 | 6.44 ± 3.37 | 3.6 ± 0.41 |
|         | Final   | 158.36 ± 30.46 | 100.52 ± 32.55 | 41.20 ± 19.53 | 98.55 ± 27.99 | 3.19 ± 1.85 | 4.51 ± 2.07 | 3.9 ± 0.74 |

As the data in Table 3 above demonstrates, our experiments show that Ig reduces plasma total cholesterol concentrations by 39.21%, triglycerides by 44.9% ($p<0,05$) and LDL by 45.58% in humans. This was accompanied by a significant increase in HDL-cholesterol of 46.852%. The CT/HDL ratio ($p<0.05$) and the blood glucose level were also reduced (32.36%; $p<0.05$). These results suggest that Ig supplementation can assist in controlling fasting and post-prandial blood glucose levels, which is typically, achieved by the 10-20% reduction in glucose response after a meal. No significant change was observed in the placebo group. Increased or abnormal cholesterol, triglycerides and LDL levels and decreased or abnormal HDL levels are known symptoms of Syndrome X and therefore control or prevent Syndrome X. Accordingly, supplementation with Ig in accordance with the teachings of the present disclosure can prevent and reduce the symptoms associated with Syndrome X. Additionally, these unexpected results obtained by Ig supplementation demonstrate that Ig supplementation provides numerous health-related benefits and effects factors that are known to cause a variety of metabolic disorders, including insulin resistance and diabetes.

Safety of Ig in Humans

Considering the wide use of Ig in the preparation of various dishes in various parts of the world, including Cameroon, its safety has been demonstrated. Additionally, our experiments further confirmed Ig's safety at the indicated dosages. Accordingly, Ig's use as a nutritional supplement at the indicated levels should be safe.

Effects of Ig Supplementation in Guinea Pigs

To further confirm the efficacy and safety of Ig to provide various health related benefits in other mammals, we performed tests to determine the effect of Ig seeds on body weight and blood lipids in Guinea pigs. Similar to the results of our experiments in humans, the results of our experiments in Guinea pigs demonstrate that the oral treatment of an aqueous extract of Ig seeds at a dose of 250 mg/kg for three weeks induced a significant decrease in weight and a significant increase in HDL cholesterol. This was accompanied by a significant decrease in plasma triglycerides and LDL cholesterol.

The study also investigated the effects of an oral administration of the crude extract of Ig on body weight and blood, liver and faeces lipids of Guinea pigs.

Ig fruits for our experiment were collected in August 2001 in a village near the town of Ebolowa in the Southern Province of Cameroon and identified in the National Herbarium, Yaounde, Cameroon. Seeds of the Ig fruits were carefully washed with water and dried for 72 hours at 50° C. in a ventilated oven. The dried seeds were then ground using an electric grinder. The resulting mixture (125 mg/ml) was used to prepare an infusion.

Normolipidemic Guinea pigs (average weight of 429.6±84.7 grams) were divided into three groups of six animals. One group was fed a standard diet with a daily oral administration of 1 ml of deionized water throughout the experimental period. This served as the normal control (Group I). The second group of animals received the standard diet with one daily administration of 1 ml palm kernel oil and 0.5ml of deionized water by and comprised the positive control group (Group II). The third group received the standard diet, 1 ml of palm kernel oil and 0.5 ml (250 mg/kg body weight) of an aqueous extract of Ig over the 3-week experimental period (Group III). The animals were weighed every 2 days, with faeces being collected throughout the experimental period. All animals were sacrificed by cervical dislocation at the end of the experimental period. Blood samples were collected into heparinized tubes for the preparation of plasma, while the livers were collected into ice for various biochemical estimations.

Total cholesterol, triglycerides, HDL-cholesterol, calcium and magnesium in plasma were measured using different commercial diagnostic kits from SIGMA Diagnostics, UK. The Friedwald Formula was used to calculate the concentration of low-density lipoprotein (LDL) in plasma. Total lipids in liver were extracted by the method of Folch et al. [9] and the liver total cholesterol content measured using the same diagnostic kit for plasma analysis.

Data was analyzed using SPSS for Windows package. Normality of the distribution was assessed using the normal plot method. Differences between groups were assessed using the one-way analyses of variance (ANOVA) test and paired Student t-test for comparison between final and initial values.

Effect of Crude Ig Extract on Body Weight

As the summarized data in Table 4 demonstrates, our experiment showed a significant reduction of the body weight in animals receiving Ig after one week of treatment (3.15±1.50%; $p<0,05$), two weeks (5.89±1.44%; $p<0,001$) and three weeks (7.74±1.42%; $p<0,001$). The body weight of the positive control group was significantly increased (8.39±1.13% ($p<0,0001$) over the experimental period.

TABLE 4

| Group | Initial | Week₁ | Week₂ | Week₃ |
| --- | --- | --- | --- | --- |
| Group I | 426.3 ± 27.59 | 430.5 ± 20.3 | 439.5 ± 19.4 | 405.5 ± 17.6 |
| Group II | 441.76 ± 64.3 | 457.1 ± 62.6 | 475.68 ± 71.5 | 478 ± 76.7*** |
| Group III | 492.56 ± 81.5 | 477 ± 63.4* | 463.6 ± 64.5** | 454.42 ± 64.3** |

*$p < 0.05$;
**$p < 0.001$;
***$p < 0.0001$ compared to Group II (positive control)

The Effect of Ig on Total Cholesterol, HDL-C and LDL-C/HDL-C Ratios

Table 5 is chart and FIG. 1 is a bar graph summarizing the data from the test we performed to demonstrate the effect of Ig on body lipids and cholesterol of Guinea pigs. Table 5 and FIG. 1 demonstrate that triglyceride levels of Ig and normal control group were lower than positive control ($p<0,05$). Although no significant difference was found between total cholesterol levels of treated and positive control Guinea pigs, HDL-cholesterol concentration was significantly higher ($p<0.01$) and LDL-c lower ($p<0.05$) for animals that received Ig compared to the positive control. The LDL-cholesterol concentration of normal control animals was also lower than that of positive control ($p<0.05$). No significant differences were found between their ratio of total cholesterol to HDL-cholesterol (T-c/HDL-c), but the LDL/HDL ratio of the positive control group was higher compared to Ig ($p<0,001$) and normal control group ($p<0.01$). The concentration of cholesterol in the liver of the treated group was 83.8±12.8 mg/dl, while that of the normal control group was 125.8±27.4 mg/dl, these values both being lower than positive control group (235.5±32.3 mg/dl).

TABLE 5

| Groups of animals | T-c/HDL | LDL-c/HDL-c | Liver Cholesterol |
| --- | --- | --- | --- |
| Group I | 1.37 ± 0.53 | 0.26 ± 0.08* | 126 ± 1.41* |
| Group II | 1.73 ± 0.84 | 0.4 ± 0.22 | 250 ± 4.88 |
| Group III | 1.10 ± 0.48 | 0.017 ± 0.007*** | 100 ± 1.97* |

*$p < 0.05$;
***$p < 0.0001$ compared to positive control

Effect of Ig on Faecal and Plasma Concentration of Calcium and Magnesium

The results of our experiments measuring the effect of Ig on faecal excretion of calcium are summarized in Table 6. Table 6 shows that Ig supplementation resulted in higher faecal calcium excretion for positive control ($P<0.05$) compared to normal control and treated groups, but the amount of magnesium excreted was higher in normal control and treated groups ($p<0.05$).

TABLE 6

| | Faecal | | Plasma | |
| --- | --- | --- | --- | --- |
| Groups | Ca | Mg | Ca | Mg |
| Group I | 6.66 ± 1.3* | 5.39 ± 0.8* | 1.93 ± 0.9 | 3.64 ± 0.3 |
| Group II | 16.34 ± 4.3 | 2.70 ± 0.3 | 3.65 ± 1.1 | 3.92 ± 0.5 |
| Group III | 8.37 ± 2.9* | 5.74 ± 1.0* | 3.38 ± 0.5 | 3.38 ± 0.5 |

*$p < 0.05$ compared to positive control

Like other soluble fibers, Ig seed fiber can bind to bile acids in the gut and carry them out of the body in the faeces, which requires the body to convert more cholesterol into bile acids, resulting in the lowering of blood cholesterol. Others studies have shown that supplementation with several grams per day of soluble fiber significantly reduced total blood cholesterol, LDL cholesterol, and triglycerides, and in some cases raised HDL cholesterol.

It should be appreciated that the effects brought about by the composition and methods of the present disclosure are a result of oral ingestion of Ig or introduction into the circulation by infusion or garvage. Additionally, the benefits and advantages of the methods and compositions of the present disclosure are most noticeable with the dilapidated Ig extract, then with the ethanol extract of Ig and finally with the ground grains of Ig. It should also be appreciated that all of the methods and compositions of the present disclosure are effective on their own or in combination with other materials and compositions.

By example and not limitation, our experiments have shown that the seed extract of Ig is effective in, among other things, weight reduction and plasma lipid modification. Accordingly, it should be appreciated by one of ordinary skill in the art that its use will retard, prevent or treat obesity and hyperlipidemia.

Effects of Ig on Alpha-Amylase Activity

The effects of crude dilapidated Irvingia gabonensis, as well as three protein fractions derived from Irvingia gabonensis on starch hydrolysis catalyzed by porcine pancreatic amylase were investigated. It was concluded that these fractions as well as the crude fraction proteins inhibit alpha-amylase activity. Based on the kinetic data and using the general velocity equation, which is valid at equilibrium for all types of inhibition in a single substrate reaction, it was concluded that the inhibitory mode is of the mixed non-competitive type. The effect of pH was also investigated and it was concluded that the inhibition was maximum at pH 6.9. Inhibition takes place when porcine pancreatic amylase (PPA) and inhibitor ($\alpha$-AI) are pre-incubated together before the substrate is added. This shows that the inhibitory PPA-$\alpha$-AI complex might be formed during the pre-incubation period.

The amounts of crude delipidated Ig extract that brought about a 50% inhibition ($IQ_{50}$) of the activities of pancreatic and salivary amylase respectively were 10.85±1.26 and 11.32±0.34 mg. These amounts were significantly reduced in the crude protein fraction, and further reduced by the glutelins, globulins and albumin fractions of Ig. The results of our experiments measuring Ig's ability to prevent pancreatic and salivary alpha-amylase activity are shown in Table 7 below.

TABLE 7

Q$_{50}$ Of Different Fractions Of Ig

|  | Dilapidated fraction | Protein fraction | Glutelins | Globulins | Albumins |
|---|---|---|---|---|---|
| IQ50 (mg) pancreatic α-amylase | 10.85 ± 1.26 | 7.21 ± 0.89 | 2.13 ± 0.10 | 1.69 ± 0.11 | 1.01 ± 0.22 |
| IQ50 (mg) salivary α-amylase | 11.32 ± 0.34 | 6.57 ± 0.91 | 3.10 ± 0.21 | 2.06 ± 0.26 | 1.12 ± 0.18 |

I claim:

1. A method for reducing weight in a mammal comprising: administering a composition containing an effective amount of glutelins isolated from a protein fraction obtained from delipidated seed of *Irvingia gabonensis* to a mammal to reduce weight in the mammal.

2. A method of claim 1, wherein reducing weight in a mammal includes reducing fat in a mammal.

3. A method of claim 1, wherein the effective amount of glutelins is from 1 g to 10 g to the mammal daily.

4. A method of claim 1, wherein the effective amount of glutelins is from 2 g to 5 g to the mammal daily.

5. A method of claim 1, wherein the effective amount of the glutelins is from 10 mg/kg of body weight of the mammal to 50 mg/kg of body weight of the mammal daily.

6. A method of claim 1, wherein the effective amount of glutelins is from 15 mg/kg of body weight of the mammal to 35 mg/kg of body weight of the mammal daily.

7. A method for reducing weight in a mammal comprising: administering a composition containing an effective amount of glutelins and globulins isolated from a protein fraction obtained from delipidated *Irvingia gabonensis* to a mammal to reduce weight in the mammal.

8. A method of claim 7, wherein reducing weight in a mammal includes reducing fat in a mammal.

9. A method of claim 7, wherein the effective amount of glutelins and globulins is from 1 g to 10 g to the mammal daily.

10. A method of claim 7, wherein the effective amount of glutelins and globulins is from 10 mg/kg of body weight of the mammal to 50 mg/kg of body weight of the mammal daily.

11. A method of claim 7, wherein the effective amount of glutelins and globulins is from 15 mg/kg of body weight of the mammal to 35 mg/kg of body weight of the mammal daily.

12. A method for reducing weight in a mammal comprising: administering a composition containing an effective amount of glutelins, globulins, and albumins isolated from a protein fraction obtained from delipidated seed of *Irvingia gabonensis* to a mammal to reduce weight in the mammal.

13. A method of claim 12, wherein reducing weight in a mammal includes reducing fat in a mammal.

14. A method of claim 12, wherein the effective amount of glutelins, globulins, and albumins is from 1 g to 10 g to the mammal daily.

15. A method of claim 12, wherein the effective amount of glutelins, globulins, and albumins is from 10 mg/kg of body weight of the mammal to 50 mg/kg of body weight of the mammal daily.

16. A method of claim 12, wherein the effective amount of glutelins, globulins, and albumins is from 15 mg/kg of body weight of the mammal to 35 mg/kg of body weight of the mammal daily.

* * * * *